US009158036B2

(12) United States Patent
Liu et al.

(10) Patent No.: US 9,158,036 B2
(45) Date of Patent: Oct. 13, 2015

(54) METHOD AND SYSTEM FOR MONITORING POWER TRANSMISSION LINE OF POWER GRID

(75) Inventors: Jianming Liu, Beijing (CN); Xiangzhen Li, Beijing (CN); Yan Zhen, Beijing (CN); Xi Chen, Beijing (CN); Lingkang Zeng, Beijing (CN); Qinghai Ou, Beijing (CN); Qingsu He, Beijing (CN)

(73) Assignee: State Grid Information & Telecommunication Branch, Beijing (CN)

( * ) Notice: Subject to any disclaimer, the term of this patent is extended or adjusted under 35 U.S.C. 154(b) by 166 days.

(21) Appl. No.: 14/124,598

(22) PCT Filed: Nov. 29, 2011

(86) PCT No.: PCT/CN2011/083170
§ 371 (c)(1),
(2), (4) Date: Dec. 6, 2013

(87) PCT Pub. No.: WO2012/167579
PCT Pub. Date: Dec. 13, 2012

(65) Prior Publication Data
US 2014/0123750 A1 May 8, 2014

(30) Foreign Application Priority Data
Jun. 10, 2011 (CN) .......................... 2011 1 0154537

(51) Int. Cl.
*G01W 1/06* (2006.01)
*G01W 1/02* (2006.01)
(Continued)

(52) U.S. Cl.
CPC ................. *G01W 1/06* (2013.01); *G01N 17/00* (2013.01); *G01W 1/02* (2013.01); *G01W 1/14* (2013.01); *H02J 13/0075* (2013.01)

(58) Field of Classification Search
None
See application file for complete search history.

(56) References Cited

U.S. PATENT DOCUMENTS

2009/0250449 A1* 10/2009 Petrenko et al. .............. 219/262
2013/0066600 A1* 3/2013 Rousselle et al. ................. 703/1
2013/0092678 A1* 4/2013 Petrenko et al. .............. 219/473

FOREIGN PATENT DOCUMENTS

CN 101038186 A 9/2007
CN 101571413 A 11/2009
(Continued)

OTHER PUBLICATIONS

Huang, G. et al., "On-line Monitoring System Design on Transmission Line Galloping," Southern Power System Technology, Study & Analysis 2009; vol. 3, No. 4; 5 pages.
(Continued)

*Primary Examiner* — Andre Allen
(74) *Attorney, Agent, or Firm* — Faegre Baker Daniels LLP

(57) ABSTRACT

A system for monitoring a power transmission line of a power grid, including a first comprehensive sensor (402, 502) disposed at the intermediate position of a power transmission line between two towers including an altimeter, a first acceleration sensor, a temperature and humidity sensor and a rainfall sensor; a second comprehensive sensor (404, 504) disposed at the cable connector of the power transmission line including a leakage current sensor, a tension sensor and a wind speed and direction sensor; and a second acceleration sensor (406, 506) disposed at the intermediate position of the power transmission line between the cable connector of the power transmission line and the first comprehensive sensor (402, 502). A method for monitoring a power transmission line of a power grid, including a step of monitoring the sag condition, wind yaw angle, motion and position tracking, flutter conditions, breeze vibration level, fatigue life and icing situation of a power transmission line. The method and system for monitoring a power transmission line of a power grid effectively prevent and reduce incidents of the power transmission line of the power grid based on sensor multi-dimensional sensing technology combined with the advantages of wireless sensor network technology.

14 Claims, 5 Drawing Sheets

(51) Int. Cl.
   *G01N 17/00* (2006.01)
   *G01W 1/14* (2006.01)
   *H02J 13/00* (2006.01)

(56) References Cited

FOREIGN PATENT DOCUMENTS

| CN | 101915596 | A |   | 12/2010 |
| CN | 201680859 | U |   | 12/2010 |
| CN | 201811758 | U |   | 4/2011 |
| CN | 102042885 | A |   | 5/2011 |
| CN | 201852598 | U |   | 6/2011 |
| CN | 102221381 | A |   | 10/2011 |
| CN | 202630939 | U | * | 12/2012 |
| CN | 101672666 | B | * | 3/2013 |
| CN | 104180852 | A | * | 12/2014 |
| CN | 204043713 | U | * | 12/2014 |
| JP | 3386966   | B2|   | 3/2003 |
| JP | 2007093342| A |   | 4/2007 |

OTHER PUBLICATIONS

Wang, K. et al., "Sag Online Monitoring System Based on Measurement of Axial Tension Transmission Lines," East China Electric Power, Mar. 2011; vol. 39, No. 3; 5 pages.

* cited by examiner

METHOD AND SYSTEM FOR MONITORING POWER TRANSMISSION LINE OF POWER GRID

FIELD OF THE INVENTION

The present application relates to a technical field of power transmission equipment and, in particular, to a method and a system for monitoring power transmission line of power grid.

BACKGROUND OF THE INVENTION

A high voltage overhead transmission line is apt to be influenced by meteorological environment (such as gale, ice and snow, etc.) and human factor and thus fails to function, thereby resulting in a damage to the equipment on the power transmission line, and influencing safe operation of the power transmission line, even severely coming to a standstill of power supply in a large area, which causes heavy losses to national economy. For example, a breeze vibration and a lead wind yaw caused by breeze are hidden troubles commonly found on the high voltage overhead line, which is the main reason of fatigue and broken strand of the high voltage overhead transmission line. The galloping of the line formed under a strong wind condition generally lasts for up to several hours, which will bring a huge destructive effect on the high voltage power transmission line. When experiencing rain and snow, the line is covered with ice, and the pulling wires of poles or towers are more likely to be frozen. The freezing on symmetric pulling wires is not balanced in most cases, which will result in an inclination of the tower or pole. This is also a huge hidden trouble on security assurance of the power transmission line.

Trouble phenomenon of the power transmission line such as breeze vibration, galloping, icing, windage yaw, dirt, lightening strike is mostly caused by the influence of local hostile meteorological environment. Our country has a vast territory, and the power transmission line has features such as the great dispersibility of dangerous points, the long distance and difficulty in monitoring and maintenance. Monitoring records provided at regular times and fixed points in a certain region by observatory are unable to reflect meteorological condition of specific power transmission line corridor completely and correctly. In addition, in case of absence of the historical meteorological data of the power transmission line corridor, there may be certain difficulties in judging, preventing and researching the breakdown of the power transmission line.

Around the Spring Festival of 2005, an extremely rare weather of freezing rain and rain and snow appears in central region of China. Especially two provinces of Hunan and Hubei are respectively suffered from a natural disaster in which the power transmission line is covered with ice in a large area, a long duration and a high intensity in 50 years. It results in equipment failures in 500 KV transformer substation of the Central China Power Grid 5 times, and tripping operations on 18 power transmission lines of 500 KV AC/DC 69 times. In January, 2008, a dozen provinces and cities in southern part of the whole country encountered a rare weather of ice and snow, and power failure and accidents appeared in a large area since the power transmission line is covered with ice, which brings an extremely serious adverse effect on people living and the society. Power facilities in regions of Hubei, Hunan, Henan, Jiangxi, Sichuan, Chongqing, Zhejiang, Anhui, Fujian, Jiangsu, etc. have suffered from a great loss. It resulted in that 36740 power lines of more than or equal to 10 KV and 2016 transformer substations of more than or equal to 35 KV were stopped, and that 310321 towers or poles of more than or equal to 10 KV were collapsed and damaged, among which there were 8381 towers or poles from 110-500 KV, thereby resulting in an insufficient power supply and appearing interruption of power supply in large area. The power utilization of 545 counties (districts) and 2,7060,000 users were affected simply in business scope of State Grid Corporation of China, among which the power supply in 80 counties (districts) was almost break-off completely. Consequently, the direct property loss was 10.45 billions CNY.

The extreme hostile weather, external force destruction, etc. have an important effect on power safety production and safety of lines and towers. Therefore, monitoring the operation status of the line and power grid fully is very important for enhancing the safety, reliability, stability, and economy of the power system.

SUMMARY OF THE INVENTION

An object of the present application is to provide a method and a system for monitoring a power transmission line of a power grid so as to monitor the operation status of the line and power grid fully.

In order to achieve the above object, there is provided in the present application a monitoring system for a power transmission line of a power grid, including a first integrated sensor, a second integrated sensor and a second acceleration sensor. The first integrated sensor is disposed at the intermediate position of a power transmission line between two towers or poles, and includes an altimeter, a first acceleration sensor, a temperature and humidity sensor and a rainfall sensor. The second integrated sensor is disposed at the cable connector of the power transmission line, and includes a leakage current sensor, a tension sensor and a wind speed and direction sensor. The second acceleration sensor is disposed at the intermediate position of the power transmission line between the cable connector of the power transmission line and the first integrated sensor.

In an embodiment, the monitoring system further includes a data processing unit, and the data processing unit includes a sag condition acquiring module, a wind yaw angle acquiring module, a motion trajectory acquiring module, a vibration level and fatigue life acquiring module, a galloping state acquiring module and an icing situation acquiring module. The sag condition acquiring module is used to acquire the sag state of a power transmission line according to the measurement result of the altimeter, the static information about the power transmission line, transmission capacity, and the microclimate conditions measured by the temperature and humidity sensor and the rainfall sensor. The wind yaw angle acquiring module is used to acquire the wind yaw angle of the power transmission line according to the measurement data from the altimeter, the first acceleration sensor and the second acceleration sensor, and the microclimate conditions measured by the temperature and humidity sensor and the rainfall sensor. The motion trajectory acquiring module is used to acquire the motion position trajectory of the power transmission line according to the measurement data from the first acceleration sensor and the second acceleration sensor. The vibration level and fatigue life acquiring module is used to acquire the breeze vibration level and fatigue life of the power transmission line according to the measurement data from the first acceleration sensor and the second acceleration sensor, the measurement data from the wind speed and direction sensor, and the measurement data from the temperature and humidity sensor. The galloping state acquiring module is configured to acquire a maximum stress situation of the power transmission line according to the measurement data from the acceleration sensors, and acquire a monitoring result of galloping state of the power transmission line by combining the maximum stress situation, the measurement data from the altimeter and the microclimate conditions. The icing situation acquiring module is configured to monitor icing situation of the power transmission line according to measurement data from the leakage current sensor and the tension sensor.

In an embodiment, the wind speed and direction sensor is an all solid state small-sized ultrasonic resonance type wind speed and direction sensor.

In an embodiment, the monitoring system further includes a video monitoring device provided on the power transmission tower or pole and transmitting the monitored information of the power transmission line to a monitoring center via wireless communication network.

In an embodiment, the monitoring system further includes a backbone node, which receives the data from the first integrated sensor, the second integrated sensor and the second acceleration sensor and transmits the data monitored by the first integrated sensor, the second integrated sensor and the second acceleration sensor via communication network.

In an embodiment, the monitoring system further includes a communication module included in the first integrated sensor, the second integrated sensor or the second acceleration sensor and used to transmit the data monitored by the first integrated sensor, the second integrated sensor or the second acceleration sensor to a monitoring center via communication network.

In an embodiment, the transmission of the data monitored by the first integrated sensor, the second integrated sensor and the second acceleration sensor conforms to multi-hops network protocol.

In an embodiment, the monitoring system further includes an optical fiber composite overhead ground wire (OPGW) laid on the power transmission line.

In an embodiment, the altimeter is a laser ranging altimeter.

In order to achieve the above object, there is provided in the present application a monitoring method for a power transmission line of a power grid. The method includes: monitoring a sag state of the power transmission line according to a measurement result from an altimeter, static information about the power transmission line, transmission capacity, and microclimate conditions measured by a temperature and humidity sensor and a rainfall sensor; monitoring a wind yaw angle of the power transmission line according to measurement data from the altimeter and an acceleration sensor as well as the microclimate conditions measured by the temperature and humidity sensor and the rainfall sensor; monitoring a motion position trajectory of the power transmission line according to the measurement data from the acceleration sensor; acquiring a maximum stress situation of the power transmission line according to the measurement data from the acceleration sensor, and acquiring a monitoring result of galloping state of the power transmission line by combining the maximum stress situation, the measurement data from the altimeter and the microclimate conditions; monitoring a breeze vibration level and a fatigue life of the power transmission line according to the measurement data from the acceleration sensor, measurement data from a wind speed and direction sensor, and measurement data from the temperature and humidity sensor; and monitoring an icing situation of the power transmission line according to measurement data from a leakage current sensor and a tension sensor.

In an embodiment, the monitoring method further includes: monitoring the power transmission line and transmitting information monitored to a monitoring center via communication network.

In an embodiment, the monitoring method further includes: receiving data monitored by the altimeter, the acceleration sensor, the wind speed and direction sensor, the temperature and humidity sensor, the leakage current sensor and the tension sensor; and transmitting the data monitored by the altimeter, the acceleration sensor, the wind speed and direction sensor, the temperature and humidity sensor, the leakage current sensor and the tension sensor to a monitoring center via communication network.

In an embodiment, monitoring the wind yaw angle of the power transmission line includes: acquiring a first wind yaw angle according to the measurement data from the altimeter, the measurement data from the acceleration sensor, and a displacement model; acquiring a second wind yaw angle according to a current height measured by the altimeter and a historical height; acquiring a third wind yaw angle according to video or image information; acquiring a fourth wind yaw angle according to wind speed and direction information and the static information about the power transmission line; and acquiring a wind yaw angle of the power transmission line by combining the first wind yaw angle, the second wind yaw angle, the third wind yaw angle and the fourth wind yaw angle.

On basis of the above technical solutions, according to one aspect of the present application, in conjunction with the advantages of wireless sensor network technology, a method and a system for monitoring a power transmission line online based on sensor multi-dimensional sensing technology are provided to realize a reliable online monitoring of the sag, the icing, the wind yaw, the wind swing and the galloping of the power transmission line. According to another aspect of the present application, the temperature sensor, acceleration sensor, temperature and humidity sensor and wind speed and direction sensor, etc. provided on the whole power transmission line, together with a sink-node on each tower or pole, form a sensor cluster, and a plurality of the clusters form a linear network and form a smart online monitoring system of the power transmission line of the whole power grid via an electric power communication network, thus effectively preventing and reducing accidents of the power transmission line of the power grid.

DETAILED DESCRIPTION

Hereinafter, the present application will be described an more detail with reference to the drawings, in which exemplary embodiments of the present application are illustrated. In the draw sings, identical reference numbers refer to identical or similar assemblies or elements.

Figure 1:
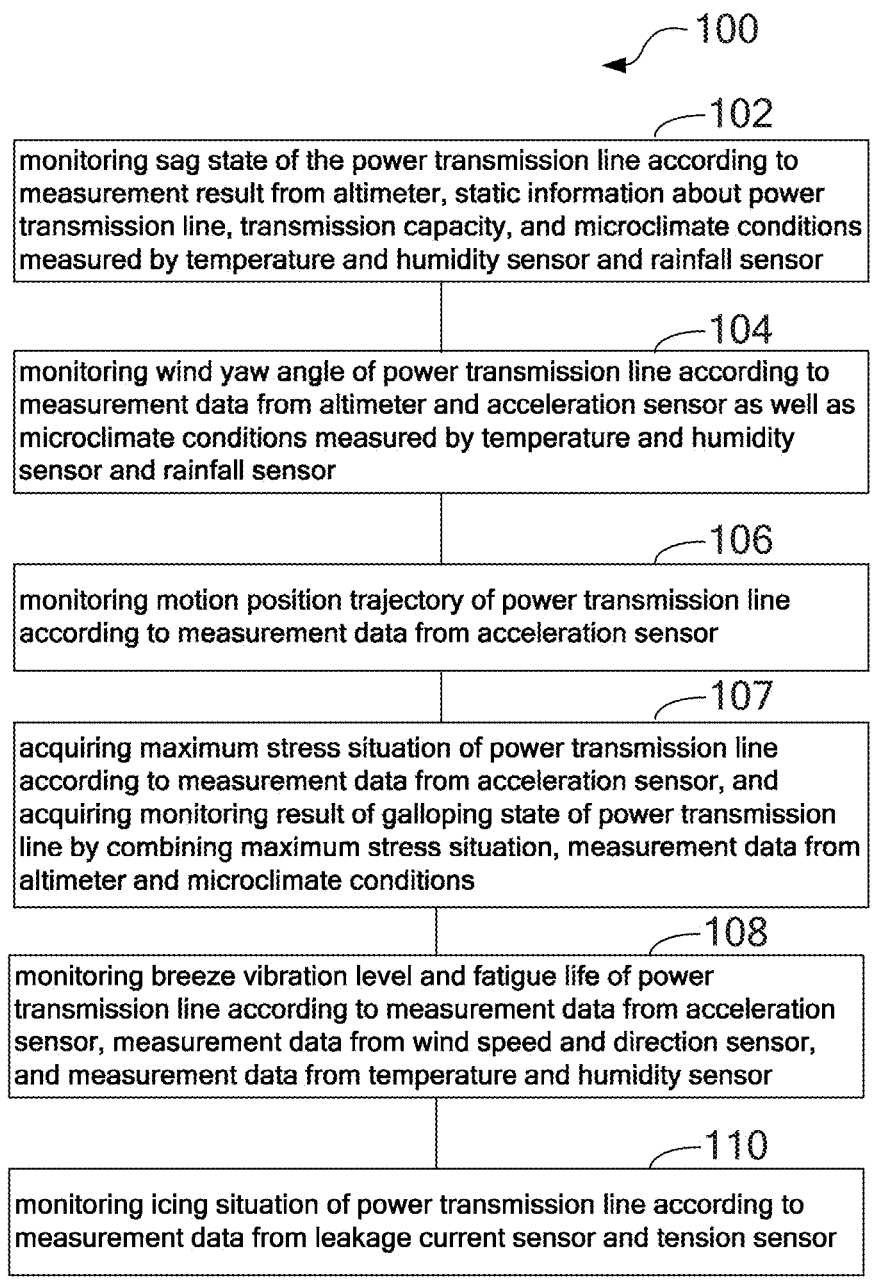
FIG. 1 is a flowchart of a method for monitoring a power transmission line of a power grid according to an embodiment in the present application.

FIG. 1 is a flowchart of a method 100 for monitoring a power transmission line of a power grid according to an embodiment in the present application.

At step 102, a sag state of a power transmission line is monitored according to the measurement result from an altimeter, the static information about the power transmission line, transmission capacity, and the microclimate conditions measured by a temperature and humidity sensor and a rainfall sensor.

At step 104, a wind yaw angle of the power transmission line is monitored according to the measurement data from the altimeter and an acceleration sensor and the microclimate conditions measured by the temperature and humidity sensor and the rainfall sensor.

At step 106, a motion position trajectory of the power transmission line is monitored according to the measurement data from the acceleration sensor.

At step 107, a maximum stress situation of the power transmission line is acquired according to the measurement data from the acceleration sensor, and a monitoring result of galloping state of the power transmission line is acquired by combining the maximum stress condition with the measurement data from the altimeter and the microclimate conditions.

At step 108, a breeze vibration level and a fatigue life of the power transmission line is monitored according to the measurement data from the acceleration sensor, the measurement data from a wind speed and direction sensor, and the measurement data from the temperature and humidity sensor.

At step 110, an icing situation of the power transmission line is monitored according to the measurement data from a leakage current sensor and a tension sensor.

It could be appreciated for those skilled in the art that, the steps in the method 100 for monitoring the power transmission line of the power grid may be carried out in any order, as long as accidents of power grid can be prevented and reduced.

Figure 2:
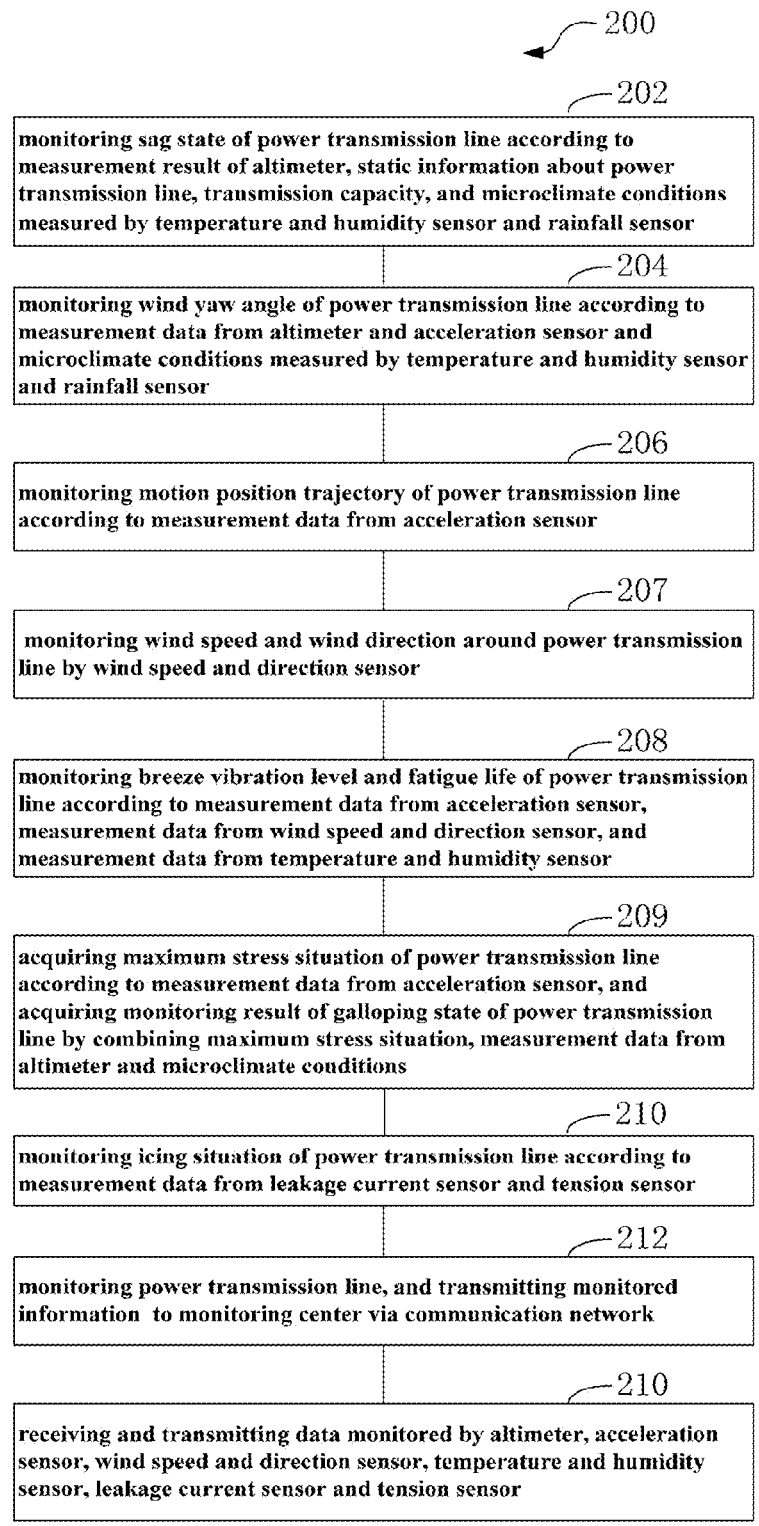
FIG. 2 is a flowchart of a method for monitoring a power transmission line of a power grid according to another embodiment in the present application.

FIG. 2 is a flowchart of a method 200 for monitoring power transmission line of a power grid according to another embodiment in the present application.

At step 202, a sag state of a power transmission line is monitored according to the measurement result of an altimeter, the static information about the power transmission line, transmission capacity, and the microclimate conditions measured by a temperature and humidity sensor and a rainfall sensor. The sag of the power transmission line is a main consideration in design and operation of a line, and must be controlled in a range of design specification since it relates to the security of operation of the line. Changes of the line operation load and surroundings all will cause a change of sag of the line, and an oversized sag will not only causes an accidental potential, but also limits the transmission capacity of the line.

In an embodiment, for a measurement to the sag of the power transmission line, a current reliable lead sag state may be obtained mainly based on the measurement of the altimeter in conjunction with a result estimated by the static information about the power transmission line, transmission capacity and the microclimate conditions, etc. The measurement result of the sag may be important information sources of state measurements on icing, wind yaw, and galloping, etc. In an embodiment, the altimeter may be a laser ranging altimeter.

At step 204, a wind yaw angle of the power transmission line is monitored according to the measurement data from the altimeter and an acceleration sensor (such as MEMS gyroscope) and the microclimate conditions measured by the temperature and humidity sensor and the rainfall sensor. In an embodiment, a first wind yaw angle may be obtained according to the measurement data from the altimeter, the measurement data from the acceleration sensor and a displacement model. A second wind yaw angle may be obtained according to the current height measured by the altimeter and the historical height. A third wind yaw angle may be obtained according to video or image information. A fourth wind yaw angle may be obtained according to wind speed and direction information and the static information about the power transmission line. Then, the wind yaw angle of the power transmission line is obtained by combination of the first wind yaw angle, the second wind yaw angle, the third wind yaw angle and the fourth wind yaw angle.

At step 206, a motion position trajectory of the power transmission line is monitored according to the measurement data from the acceleration sensor. When the lead is blown by side gust, the swing trajectory thereof may be simplified as a pendulum motion, and usually three phase lines are swung in the same manner. When encountering a complex meteorological situation of a mixed type including a side gust and a vertical shear wind, some two phase lines may move towards each other, thus resulting in occurrence of short circuit accident when they are excessively close to each other. A lateral acceleration of the lead may be monitored in real time via a three-axis acceleration sensor provided on the power transmission line, and the motion position trajectory of the lead may be acquired through a quadratic integral. Thus, it is possible to present warning of potential abnormal closeness between leads by systematically synthesizing motion trajectory of the sensors for respective phases at a same time.

At step 207, the wind speed and direction sensor may monitor the wind speed and the wind direction around the power transmission line. In an embodiment, the wind speed and direction sensor may be an all solid state small-sized ultrasonic resonance type wind speed and direction sensor, which is used to measure the wind speed and the wind direction around the power transmission line.

The wind yaw of lead calculated via the acceleration sensor provided on the power transmission line and the measurement data from the wind speed and direction sensor may provide actual measurement foundation for designing the power transmission line and checking the wind yaw, and may assist the operation department to find points of failure. In addition, it may be possible to, by a monitoring center, observe, record, and collect the meteorological data of the region where the power transmission line passes, gather operation data, improve a computation method of wind yaw, and meanwhile correctly record a maximum instantaneous wind speed, a wind pressure nonuniform coefficient, a lead motion trajectory under fresh gale etc. of the tower or pole on the power transmission line, so as to provide technical data for formulating a reasonable design criteria.

At step 208, a breeze vibration level and a fatigue life of the power transmission line is monitored according to the measurement data from the acceleration sensor, the measurement data from a wind speed and direction sensor, and the measurement data from the temperature and humidity sensor. For example, three-dimensional acceleration sensor is used to monitor the lead vibration situation, analyze and record the vibration frequency and amplitude of the lead, and in conjunction with microclimate environment parameters such as wind speed, wind direction, air temperature, humidity etc. around the line as well as mechanics performance parameters of the lead, analyze and determine the breeze vibration level of the line and the fatigue life of the lead online.

In the operation of the lead, since a vibration is superimposed on a static tension, the lead is suffered from a series of complex loads including several kinds of stress level components, and within a same period of time in the operation of the lead, the components have different cycle times of vibration. The cumulative damage theory may be applied to estimate a fatigue service life of the lead suffered from the series of complex loads. A stress block diagram is a basis of cumulative frequency curve, such that the cycle times of different stress levels in a same period of time may be estimated by analyzing vibration signal data of the power transmission line in time domain and frequency domain. Meanwhile, the magnitude of vibration on each frequency component may be observed, thus preventing a possible resonance on the power transmission line. The fatigue life may be calculated through estimation. An overhaul suggestion may be provided referring to the predetermined results and a suggestion, forewarning and alarm value set in an expert knowledge database.

At step 209, a maximum stress situation of the power transmission line is acquired according to the measurement data from the acceleration sensor, and a monitoring result of galloping state of the power transmission line is acquired by combining the maximum stress situation, the measurement data from the altimeter and the microclimate conditions. For example, three-dimensional acceleration sensor nodes are installed on one lead at multiple locations to monitor the galloping situation of the lead, to collect information of three-axis acceleration, and to analyze a longitudinal and lateral galloping half-wave number of the galloping line and calculate relevant parameters of the motion trajectory of the lead according to a calculation and analysis of the acceleration of the monitoring point, basic information of the line and a three-degree-of-freedom data model of the galloping of the lead, thereby determining whether the galloping harm will occur or not according to historical experience and relevant model. If the galloping harm will occur, warning message is sent so as to avoid an accident occurrence such as a discharge between phases, a collapse of the tower, etc.

When the power transmission line encounters a gale angled horizontally relative to the line by an angle larger than 45 degrees, the whole lead will be twisted and swung under the strong wind power and mechanical stress of the lead itself, and such twist and swing of the whole lead increases gradually with the lasting wind power, so that an elliptical motion trajectory is formed gradually. When the twist is intensified and causes the lead to fluctuate greatly up and down at a lower frequency, the twist and swing of the lead is then not obvious, and the whole lead is in a directional undulating motion. When the wind power is weakened, the lead will gradually return from up-down fluctuation to a twist and swing motion, and then be weakened gradually till stop. It could be concluded according to the characteristics of the galloping that, at the earlier stage and later stage of the fierce motion of the galloping, the swing motion makes a major contribution to the motion trajectory of the line. Therefore, monitoring in real time the angle of swing of the power transmission line or the amplitude of swing of some point on the power transmission line enables the line to be monitored and pre-warned better.

The motion trajectory of some point on the lead may be depicted by the acceleration sensor, and position data may be acquired from a double integral of the acceleration data. In addition, since the acceleration data is discrete, and thus may be processed through an approximate integration. Through calculation, the maximum motion distance of the lead may be acquired precisely, and the maximum stress situation of the lead may be approximately deduced from the measured maximum acceleration, thereby providing a guiding data of a damage probability of the lead.

Since the galloping of the lead is influenced by various parameters, in the actual system, by combining the galloping monitoring of the lead with information such as microclimate, altimeter and tower video, a reasonable multi-source information fusion model is designed, and a reliable monitoring result of the galloping state is acquired.

At step 210, an icing situation of the power transmission line is monitored according to the measurement data from a leakage current sensor and a tension sensor. For example, insulator leakage current sensor and tension sensor nodes may be installed on the insulator of the power transmission tower or pole to collect data of tension, weight, etc., and calculation and determination may be made according to the corresponding relation between tension, weight and icing situation. In addition, the icing situation of the line may also be monitored in real time by measuring the sag of the line in real time.

Whether it is possible to be covered with ice or not also may be determined by measuring parameters of ambient temperature, humidity, wind speed, wind direction and rainfall etc. in real time. A tension sensor may be initiated to make an insulator tension measurement if there exists probability of icing, so as to correctly determine whether there is an icing phenomenon or not. If there is no probability of icing, the tension measurement with high power consumption will not be initiated, thereby prolonging a life of a battery for the insulator leakage current sensor and tension sensor nodes.

At step 212, the power transmission line is monitored, and the monitored information is transmitted to a monitoring center via communication network. For example, a video monitoring device may be installed on important large-span power transmission towers or poles, and information of photo, video etc. may be transmitted to the monitoring center via a wireless communication network. Thus, the monitoring center can get at any time around the clock the situation of the power transmission line, such as the situation of formation and development of icing, etc. In addition, by analyzing and comparing the current image information captured by video monitoring device on the tower with the historical information, sag and icing situation of the line may be determined further. A proper adjustment could be proceed in time according to microclimate measurement data, for example, increasing electric current in the line to enhance the temperature of the line, thereby preventing the lead from icing.

At step 214, the data monitored by the altimeter, the acceleration sensor, the wind speed and direction sensor, the temperature and humidity sensor, the leakage current sensor and the tension sensor are received, and the data monitored by the altimeter, the acceleration sensor, the wind speed and direction sensor, the temperature and humidity sensor, the leakage current sensor and the tension sensor is transmitted to a monitoring center via communication network.

Since the power transmission line has a large distribution range and a large span distance, in order to ensure an effective transmission of the sensed information and avoid losing the information, multi-hops network protocol may be adopted in sensor network, and the network has a farther information transmission distance via multi-hops communication relay manner. Remote transmission of sensed information is realized by power private communication network or with the help of public mobile communication network, thereby providing a more flexible, high speed and convenient information transmission service, ensuring the efficient unimpeded information transmission, and providing a reliable and excellent transmission service for the communication between the power transmission line on site and the background monitoring center. According to application scenarios, the system network topology may be designed as chain shaped cluster type structure, as shown in FIG. 3.

Figure 3:
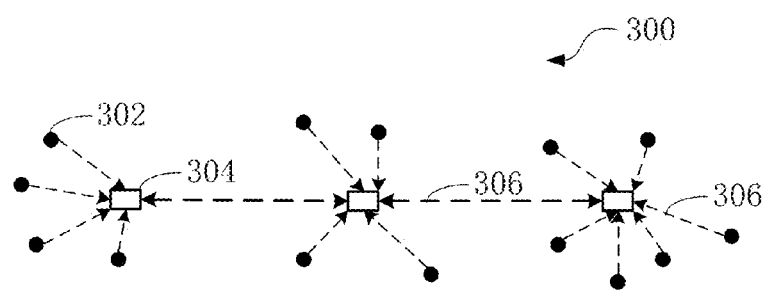
FIG. 3 is a structural schematic view of system network topology according to an embodiment in the present application.

In FIG. 3, sensing nodes 302, backbone nodes 304, and communication links 306 are included. The sensing node 302 may be provided with various sensors such as altimeter, acceleration sensor, etc. In an embodiment, the backbone node 304 may be provided on the power transmission tower or pole to collect sensing data from each sensing node 302 in communication range thereof, and transmit it to the background monitoring center via communication network. In an embodiment, a one-way communication link 306 may be provided between the sensing node 302 and the backbone node 304, and the backbone node 304 could support a plurality of sensing nodes 302, e.g., 256 sensing nodes. In an embodiment, a two-way communication link 306 may be provided for the communication between the backbone nodes 304. The backbone nodes 304 may form a chain shaped topology multi-hops network. In another embodiment, a communication module may be added on a certain sensing node 302, so as to directly transmit data from the sensors to the monitoring center via communication network. In an embodiment, the communication network may be TD-SCDMA, GSM, etc., and may be connected directly to 3G mobile communication network, or may be connected to optical fiber composite overhead ground wire (OPGW) optical network for appropriate towers or poles.

It could be appreciated for those skilled in the art that, steps 202-212 in the method 200 for monitoring the power transmission line of the power grid may be carried out in any order, as long as accidents of power grid can be prevented and reduced.

Figure 4:
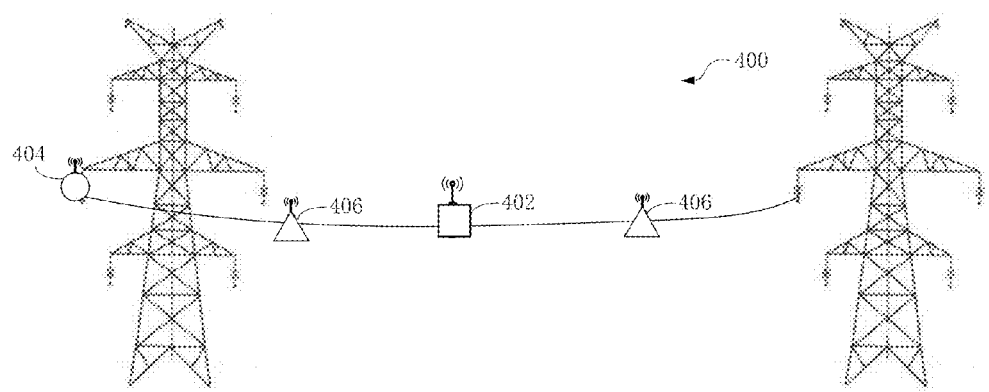
FIG. 4 is a structural schematic view of a system for monitoring a power transmission line of a power grid according to an embodiment in the present application.

FIG. 4 is a structural schematic view of a system 400 for monitoring a power transmission line of a power grid according to an embodiment in the present application. The system 400 for monitoring the power transmission line of the power grid includes a first integrated sensor 402, a second integrated sensor 404 and a second acceleration sensor 406.

The first integrated sensor 402 is disposed at the intermediate position of a power transmission line between two towers or poles, and includes an altimeter, a first acceleration sensor, a temperature and humidity sensor and a rainfall sensor.

The second integrated sensor 404 is disposed at the cable connector of the power transmission line, and includes a leakage current sensor, a tension sensor and a wind speed and direction sensor.

The second acceleration sensor 406 is disposed at the intermediate position of the power transmission line between the cable connector of the power transmission line and the first integrated sensor.

Figure 5:
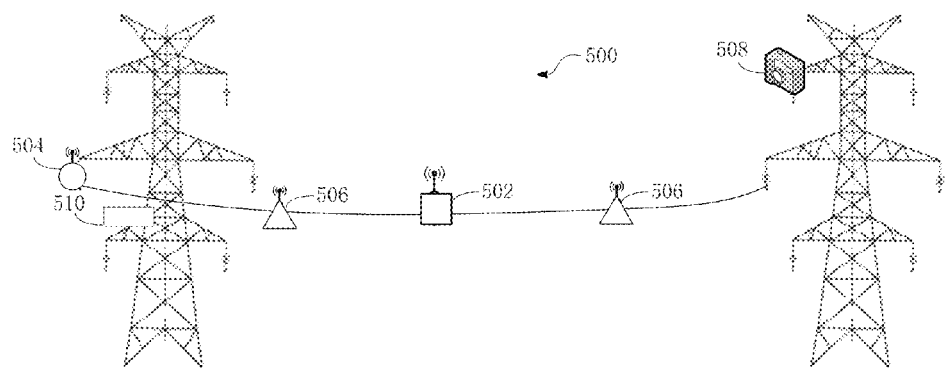
FIG. 5 is a structural schematic view of a system for monitoring a power transmission line of a power grid according to another embodiment in the present application.

FIG. 5 is a structural schematic view of a system 500 for monitoring a power transmission line of a power grid according to another embodiment in the present application. The system 500 for monitoring the power transmission line of the power grid includes a first integrated sensor 502, a second integrated sensor 504, second acceleration sensors 506, a video monitoring device 508 and a backbone node 510.

The first integrated sensor 502 is disposed at the intermediate position of a power transmission line between two towers or poles, and includes an altimeter, a first acceleration sensor, a temperature and humidity sensor and a rainfall sensor. In an embodiment, the altimeter may be a laser ranging altimeter. The first integrated sensor 502 may further include an energy supply module, a signal adjustment module, an A/D converting module, a data processing unit and a data transmission module, as shown in FIG. 6.

The second integrated sensor 504 is disposed at the cable connector of the power transmission line, and includes a leakage current sensor, a tension sensor and a wind speed and direction sensor. In an embodiment, the wind speed and direction sensor is an all solid state small-sized ultrasonic resonance type wind speed and direction sensor. The second integrated sensor 504 may further include an energy supply module, a signal adjustment module, an A/D converting module, a data processing unit and a data transmission module, as shown in FIG. 7.

Figure 6:
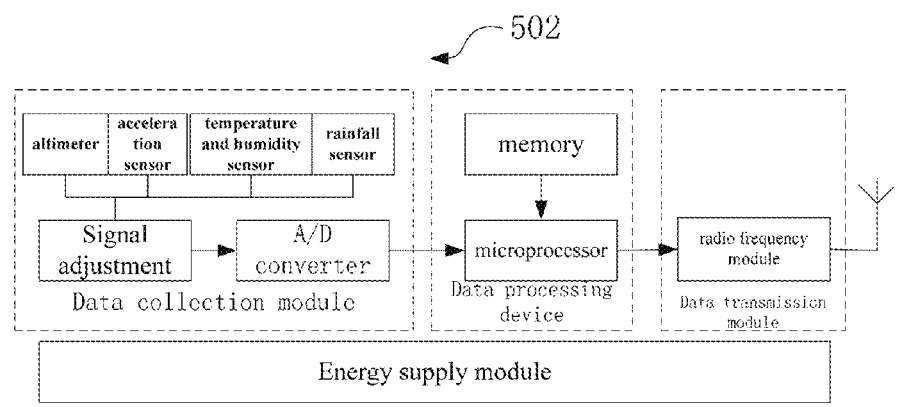
FIG. 6 is a structural schematic view of a first integrated sensor according to an embodiment in the present application.
Figure 7:
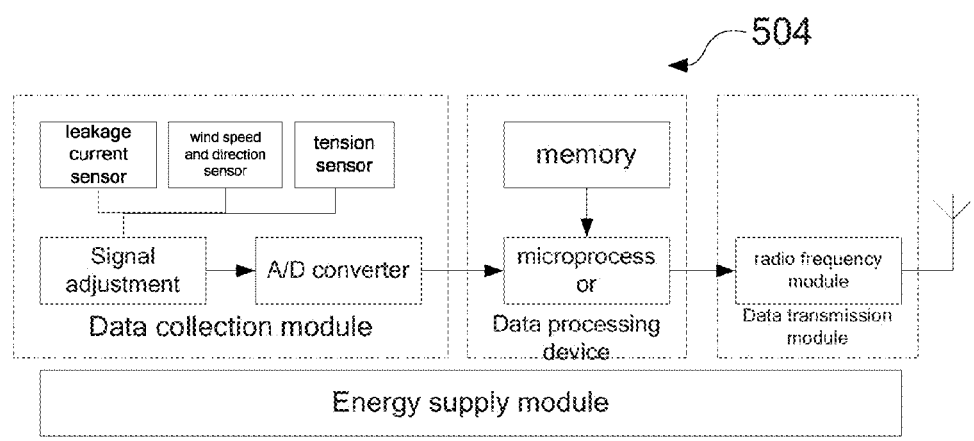
FIG. 7 is a structural schematic view of a second integrated sensor according to an embodiment in the present application.
Figure 8:
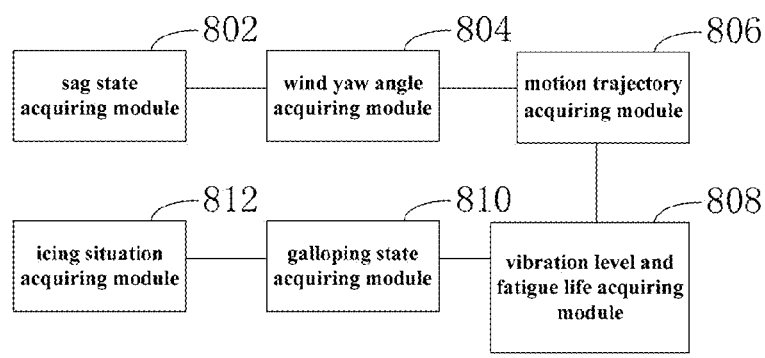
FIG. 8 is a structural schematic view of a data processing unit according to an embodiment in the present application.

The data processing unit in the first integrated sensor 502 and the second integrated sensor 504 as shown in FIGS. 6 and 7 may include a sag state acquiring module 802, a wind yaw angle acquiring module 804, a motion trajectory acquiring module 806, a vibration level and fatigue life acquiring module 808, a galloping state acquiring module 810 and/or an icing situation acquiring module, as shown in FIG. 8. The sag state acquiring module 802 is used to acquire the sag state of a power transmission line according to the measurement result of the altimeter, the static information about the power transmission line, transmission capacity, and the microclimate conditions measured by the temperature and humidity sensor and the rainfall sensor. The wind yaw angle acquiring module 804 is used to acquire the wind yaw angle of the power transmission line according to the measurement data from the altimeter and the first and second acceleration sensors, and the microclimate conditions measured by the temperature and humidity sensor and the rainfall sensor. The motion trajectory acquiring module 806 is used to acquire the motion position trajectory of the power transmission line according to the measurement data from the first acceleration sensor and the second acceleration sensor. The vibration level and fatigue life acquiring module 808 is used to acquire the breeze vibration level and fatigue life of the power transmission line according to the measurement data from the first acceleration sensor and the second acceleration sensor, the measurement data from the wind speed and direction sensor, and the measurement data from the temperature and humidity sensor. The galloping state acquiring module 810 is used to acquire the maximum stress situation of the power transmission line according to the measurement data from the acceleration sensors, and acquire the monitoring results of galloping state of the power transmission line by combining the maximum stress situation, the measurement data from the altimeter and the microclimate conditions. The icing situation acquiring module 812 is used to monitor the icing situation of the power transmission line according to the measurement data from the leakage current sensor and the tension sensor. In an embodiment, the data processing unit also may be included in the backbone node 510 or the background monitoring center.

The second acceleration sensor 506 is disposed at the intermediate position of the power transmission line between the cable connector of the power transmission line and the first integrated sensor. Three acceleration sensors may be provided on each power transmission line, specifically, one being integrated in the first integrated sensor 502, and the other two (such as the second acceleration sensor 506) being provided at two opposite sides of the first integrated sensor 502 and located at the middle position between the cable connector of the power transmission line and the first integrated sensor 502.

The video monitoring device 508 is provided on the power transmission tower or pole and transmits the monitored information of the power transmission line to a monitoring center via wireless communication network.

The backbone node 510 receives the data from the first integrated sensor 502, the second integrated sensor 504, the second acceleration sensor 506 and the video monitoring device 508, and transmits the data monitored by the first integrated sensor 502, the second integrated sensor 504, the second acceleration sensor 506 and the video monitoring device 508 via communication network.

In an embodiment, the first integrated sensor 502, the second integrated sensor 504, the second acceleration sensor 506 or the video monitoring device 508 may include a communication module, which is used to directly transmit the data monitored by the first integrated sensor 502, the second integrated sensor 504, the second acceleration sensor 506 or the video monitoring device 508 to a monitoring center via communication network.

In an embodiment, the transmission of the data monitored by the first integrated sensor 502, the second integrated sensor 504, the second acceleration sensor 506 and the video monitoring device 508 may conform to the multi-hops network protocol. The communication network may be TD-SCDMA network. In an embodiment, the power transmission tower or pole may also be connected to an optical fiber composite overhead ground wire (OPGW).

On basis of the above description, according to one aspect of the present application, in conjunction with the advantages of wireless sensor network technology, a method and a system for monitoring a power transmission line online based on sensor multi-dimensional sensing technology are provided to realize a reliable online monitoring of the sag, the icing, the wind yaw, the wind swing and the galloping of the power transmission line. The temperature sensor, acceleration sensor, temperature and humidity sensor and wind speed and direction sensor, etc. provided on the whole power transmission line, together with a sink-node on each tower or pole, form a sensor cluster, and a plurality of the clusters form a linear network and form a smart online monitoring system of the power transmission line of the whole power grid via an electric power communication network, thus effectively preventing and reducing accidents of the power transmission line of the power grid.

The description of the present application is given for the exemplary and illustrative purpose, but is not exhaustive or does not limit the present application to those disclosed. Many modifications and variations are apparent to those skilled in the art. The embodiment is chosen and described in order to illustrate the principle and the practical application of the present application better, and enable those skilled in the art to understand the present application so as to design various embodiments for specific uses with various modifications.

What is claimed is:

1. A monitoring system for a power transmission line of a power grid, comprising:
    a first integrated sensor disposed at an intermediate position of a power transmission line between two towers or poles, and comprising an altimeter, a first acceleration sensor, a temperature and humidity sensor and a rainfall sensor;
    a second integrated sensor disposed at a cable connector of the power transmission line, and comprising a leakage current sensor, a tension sensor and a wind speed and direction sensor; and
    a second acceleration sensor disposed at an intermediate position of a power transmission line between the cable connector of the power transmission line and the first integrated sensor.

2. The monitoring system according to claim 1, further comprising a data processing unit, wherein the data processing unit comprises:
    a sag state acquiring module configured to acquire a sag state of a power transmission line according to a measurement result from the altimeter, static information about the power transmission line, transmission capacity, and microclimate conditions measured by the temperature and humidity sensor and the rainfall sensor;
    a wind yaw angle acquiring module configured to acquire a wind yaw angle of the power transmission line according to measurement data from the altimeter, the first acceleration sensor and the second acceleration sensor, and the microclimate conditions measured by the temperature and humidity sensor and the rainfall sensor;
    a motion trajectory acquiring module configured to acquire a motion position trajectory of the power transmission line according to the measurement data from the first acceleration sensor and the second acceleration sensor;
    a vibration level and fatigue life acquiring module configured to acquire a breeze vibration level and fatigue life of the power transmission line according to the measurement data from the first acceleration sensor and the second acceleration sensor, measurement data from the wind speed and direction sensor, and measurement data from the temperature and humidity sensor;
    a galloping state acquiring module configured to acquire a maximum stress situation of the power transmission line according to the measurement data from the acceleration sensors, and acquire a monitoring result of galloping state of the power transmission line by combining the maximum stress situation, the measurement data from the altimeter and the microclimate conditions; and
    an icing situation acquiring module configured to monitor icing situation of the power transmission line according to measurement data from the leakage current sensor and the tension sensor.

3. The monitoring system according to claim 1, wherein the wind speed and direction sensor is an all solid state small-sized ultrasonic resonance type wind speed and direction sensor.

4. The monitoring system according to claim 1, further comprising:
    a video monitoring device provided on the power transmission tower or pole, and configured to transmit monitored information of the power transmission line to a monitoring center via wireless communication network.

5. The monitoring system according to claim 1, further comprising:
    a backbone node configured to receive data from the first integrated sensor, the second integrated sensor and the second acceleration sensor, and transmit the data monitored by the first integrated sensor, the second integrated sensor and the second acceleration sensor via communication network.

6. The monitoring system according to claim 1, further comprising:
    a communication module included in the first integrated sensor, the second integrated sensor or the second acceleration sensor, and configured to transmit the data monitored by the first integrated sensor, the second integrated sensor or the second acceleration sensor to a monitoring center via communication network.

7. The monitoring system according to claim 5, wherein transmission of the data monitored by the first integrated sensor, the second integrated sensor and the second acceleration sensor conforms to multi-hops network protocol.

8. The monitoring system according to claim 1, further comprising:
an optical fiber composite overhead ground wire (OPGW) laid on the power transmission line.

9. The monitoring system according to claim 1, wherein the altimeter is a laser ranging altimeter.

10. A monitoring method for a power transmission line of a power grid, comprising:
monitoring a sag state of the power transmission line according to a measurement result from an altimeter, static information about the power transmission line, transmission capacity, and microclimate conditions measured by a temperature and humidity sensor and a rainfall sensor;
monitoring a wind yaw angle of the power transmission line according to measurement data from the altimeter and an acceleration sensor as well as the microclimate conditions measured by the temperature and humidity sensor and the rainfall sensor;
monitoring a motion position trajectory of the power transmission line according to the measurement data from the acceleration sensor;
acquiring a maximum stress situation of the power transmission line according to the measurement data from the acceleration sensor, and acquiring a monitoring result of galloping state of the power transmission line by combining the maximum stress situation, the measurement data from the altimeter and the microclimate conditions;
monitoring a breeze vibration level and a fatigue life of the power transmission line according to the measurement data from the acceleration sensor, measurement data from a wind speed and direction sensor, and measurement data from the temperature and humidity sensor; and
monitoring an icing situation of the power transmission line according to measurement data from a leakage current sensor and a tension sensor.

11. The monitoring method according to claim 10, further comprising:
monitoring the power transmission line and transmitting information monitored to a monitoring center via communication network.

12. The monitoring method according to claim 10, further comprising:
receiving data monitored by the altimeter, the acceleration sensor, the wind speed and direction sensor, the temperature and humidity sensor, the leakage current sensor and the tension sensor; and
transmitting the data monitored by the altimeter, the acceleration sensor, the wind speed and direction sensor, the temperature and humidity sensor, the leakage current sensor and the tension sensor to a monitoring center via communication network.

13. The monitoring method according to claim 10, wherein monitoring the wind yaw angle of the power transmission line comprises:
acquiring a first wind yaw angle according to the measurement data from the altimeter, the measurement data from the acceleration sensor, and a displacement model;
acquiring a second wind yaw angle according to a current height measured by the altimeter and a historical height;
acquiring a third wind yaw angle according to video or image information;
acquiring a fourth wind yaw angle according to wind speed and direction information and the static information about the power transmission line; and
acquiring a wind yaw angle of the power transmission line by combining the first wind yaw angle, the second wind yaw angle, the third wind yaw angle and the fourth wind yaw angle.

14. The monitoring system according to claim 6, wherein transmission of the data monitored by the first integrated sensor, the second integrated sensor and the second acceleration sensor conforms to multi-hops network protocol.

* * * * *